(12) United States Patent
Liu et al.

(10) Patent No.: US 7,935,833 B2
(45) Date of Patent: May 3, 2011

(54) COMPOUND CONTAINING CARBOXYLATE ESTER AND N2S2 LIGAND BI-FUNCTIONAL GROUPS AND MANUFACTURING METHOD THEREOF

(75) Inventors: Show-Wen Liu, Shetou Township, Changhua County (TW); Tsyh-Lang Lin, Bade (TW); Cheng-Fang Hsu, Toufen Township, Miaoli County (TW); Cheng-Hsien Lin, Taipei (TW); Tsai-Yueh Luo, Longtan Township, Taoyuan County (TW); Lie-Hang Shen, Jhongli (TW); Haw-Jan Chen, Taoyuan (TW)

(73) Assignee: Atomic Energy Council-Institute of Nuclear Energy Research, Taoyuan (TW)

( * ) Notice: Subject to any disclaimer, the term of this patent is extended or adjusted under 35 U.S.C. 154(b) by 62 days.

(21) Appl. No.: 12/203,214

(22) Filed: Sep. 3, 2008

(65) Prior Publication Data

US 2010/0056804 A1    Mar. 4, 2010

(51) Int. Cl.
*C07D 207/46* (2006.01)
(52) U.S. Cl. ...................................................... 548/542
(58) Field of Classification Search ............... 548/302.7, 548/541; 514/394, 421
See application file for complete search history.

*Primary Examiner* — Kamal A Saeed
*Assistant Examiner* — Kristin Bianchi
(74) *Attorney, Agent, or Firm* — Ming Chow; Sinorica, LLC

(57) ABSTRACT

A compound containing carboxylate ester and N2S2 ligand bi-functional groups and a manufacturing method thereof are disclosed. The S in the N2S2 ligand of the compound containing carboxylate ester and N2S2 ligand bi-functional groups includes a protective group so as to avoid to be oxidized and easy storage. In a complex reaction, the protective group is automatically released As to the active carboxylate ester, it is for reacting with compounds having amino groups such as amines, amino acids, peptides, or protein etc while the N2S2 ligand is for bonding with technetium or rhenium so as to form neutral complex. The compound containing carboxylate ester and N2S2 ligand bi-functional groups is applied to radiopharmaceuticals such as contrast agents for tissues and target agents.

11 Claims, 2 Drawing Sheets

COMPOUND CONTAINING CARBOXYLATE ESTER AND N2S2 LIGAND BI-FUNCTIONAL GROUPS AND MANUFACTURING METHOD THEREOF

BACKGROUND OF THE INVENTION

The present invention relates to a compound containing two functional groups and a manufacturing method thereof, especially to a compound containing carboxylate ester and N2S2 ligand bi-functional groups and a manufacturing method thereof that react with target material with amino-group as well as technetium or rhenium so as to form radiopharmaceuticals to be applied to contrast agents for tissues, target agents for diseases, or diagnosis devices.

The human cells have specific receptors on their surface so as to bind corresponding amines, amino acids, peptides, or protein. By means of such specificity, the compounds with these amino groups are labeled with radioactive nuclides. Once the compounds containing these amino groups entering human bodies, they are brought to specific organs or tissues so as to achieve purposes such as diagnostic imaging or disease treatment. For example, apoptosis is highly related to treatment of a plurality of diseases.

Thus Annexin-V labeled with radionuclides applied to research of apoptosis has received a lot of attention. If the protein or peptide is going to be labeled with technetium-99 m (Tc-99 m), the compound containing two functional groups is used for labeling protein with Tc-99 m. S-Hynic is a common compound having two functional groups to be used. Besides an active carboxylic ester group that reacts with protein or peptides to generate a strong amide linkage, it includes pyridinyl and hydrazo groups that react with Tc-99 m. However, S-Hynic is photosensitive substance so that it is light degraded. Moreover, the S-Hynic has low valency so that it requires addition of auxiliary substance such as tricine and this is not convenient in use. Thus there is a need to find other compounds containing two functional groups with stable physical properties and convenient to use.

In order to overcome above shortages of conventional compounds containing two functional groups, the present invention provides a compound containing carboxylate ester and N2S2 ligand bi-functional groups and a manufacturing method thereof. The compound containing carboxylate ester and N2S2 ligand bi-functional groups not only reacts with alcohols and amines but also with $ReO^{3+}$ or $TcO^{3+}$ to be applied to protein and peptide labeling with technetium or rhenium. Furthermore, the compound containing carboxylate ester and N2S2 ligand bi-functional groups has feature of photostability so that it is easy to be operated and used. Moreover, there is no need to add auxiliary chelating agents during the processes so that both reaction processes and the cost are reduced.

SUMMARY OF THE INVENTION

Therefore it is a primary object of the present invention to provide a compound containing carboxylate ester and N2S2 ligand bi-functional groups and a manufacturing method thereof. The compound containing carboxylate ester and N2S2 ligand bi-functional groups not only reacts with alcohols and amines but also bonds with $ReO^{3+}$ or $TcO^{3+}$ so as to be applied to labeling of proteins and peptides with Tc or Re.

It is another object of the present invention to provide a compound containing carboxylate ester and N2S2 ligand bi-functional groups and a manufacturing method thereof. The compound containing carboxylate ester and N2S2 ligand bi-functional groups has photostability so that it is easy to be operated and used under environment with light.

It is a further object of the present invention to provide a compound containing carboxylate ester and N2S2 ligand bi-functional groups and a manufacturing method thereof. While using the compound containing carboxylate ester and N2S2 ligand bi-functional groups, there is no need to add auxiliary chelating agents during the processes so that both reaction processes and the cost are reduced.

In order to achieve above objects, the compound containing carboxylate ester and N2S2 ligand bi-functional groups of the present invention includes:

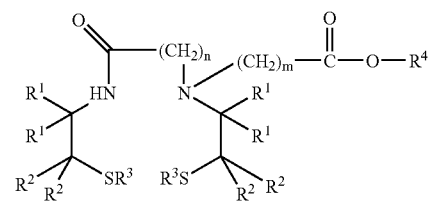

wherein $R^1$=H, $CH_3$; $R^2$=H, $CH_3$; $R^3$=$CPh_3$, $CH_2C_6H_4OCH_3$, $COC_6H_5$;

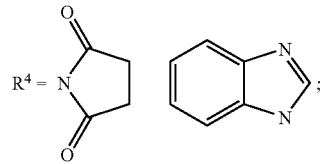

$n=1\sim3$; and $m=1\sim9$

The manufacturing method of the compound containing carboxylate ester and N2S2 ligand bi-functional groups comprising the steps of:

(1) reacting $NH_2CR^1_2CR^2_2SH$ with a protective agent to form $NH_2CR^1_2CR^2_2SR^3$ (2) carrying out an amidation reaction between $NH_2CR^1_2CR^2_2SR^3$ and $X(CH_2)_nCOX$ to form

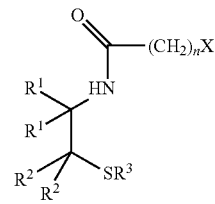

(3) undergoing a substitution reaction between

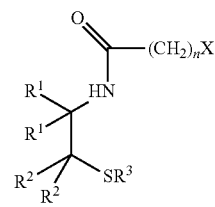

and $NH_2CR^1{}_2CR^2{}_2SR^3$ to form

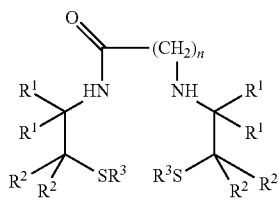

(4) carrying out a substitution reaction between

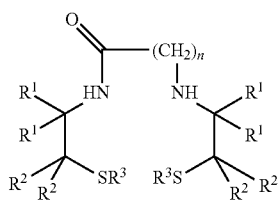

and $Br(CH_2)mCOOH$ to form

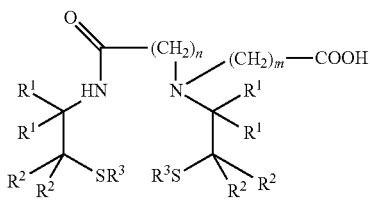

(5) dehydrating N,N'-dicyclohexyldicarbodiimide to get

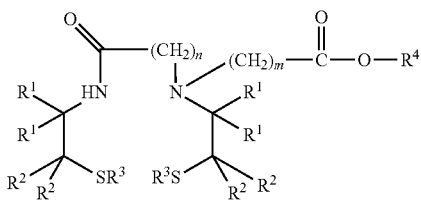

wherein $R^1$=H, $CH_3$; $R^2$=H, $CH_3$; $R^3$=$CPh_3$, $CH_2C_6H_4OCH_3$, $COC_6H_5$;

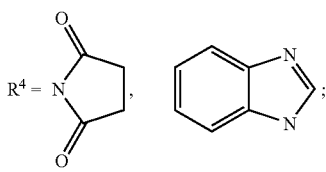

n=1~3; m=1~9 while X is halogen atom

BRIEF DESCRIPTION OF THE DRAWINGS

The structure and the technical means adopted by the present invention to achieve the above and other objects can be best understood by referring to the following detailed description of the preferred embodiments and the accompanying drawings, wherein.

DETAILED DESCRIPTION OF THE PREFFERED EMBODIMENT

A compound containing carboxylate ester and N2S2 ligand bi-functional groups according to the present invention includes:

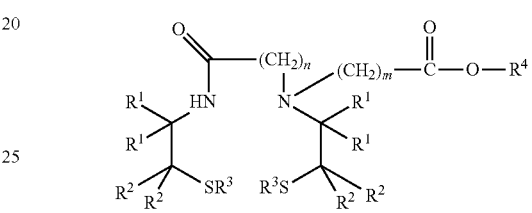

wherein $R^1$=H, $CH_3$; $R^2$=H, $CH_3$; $R^3$=$CPh_3$, $CH_2C_6H_4OCH_3$, $COC_6H_5$;

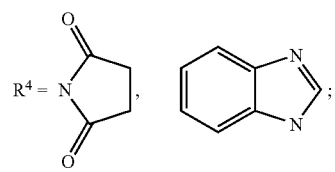

n=1~3; and m=1~9.

while when n and m=1, and $R^4$=

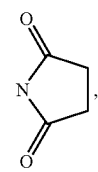

the compound containing carboxylate ester and N2S2 ligand bi-functional groups is Succinimidyl 3,6-diaza-5-oxo-3-[2-((triphenylmethyl)thio)ethyl]-8-[(triphenylmethyl)thio]octanoate, abbreviated as SOCTA.

Figure 1:
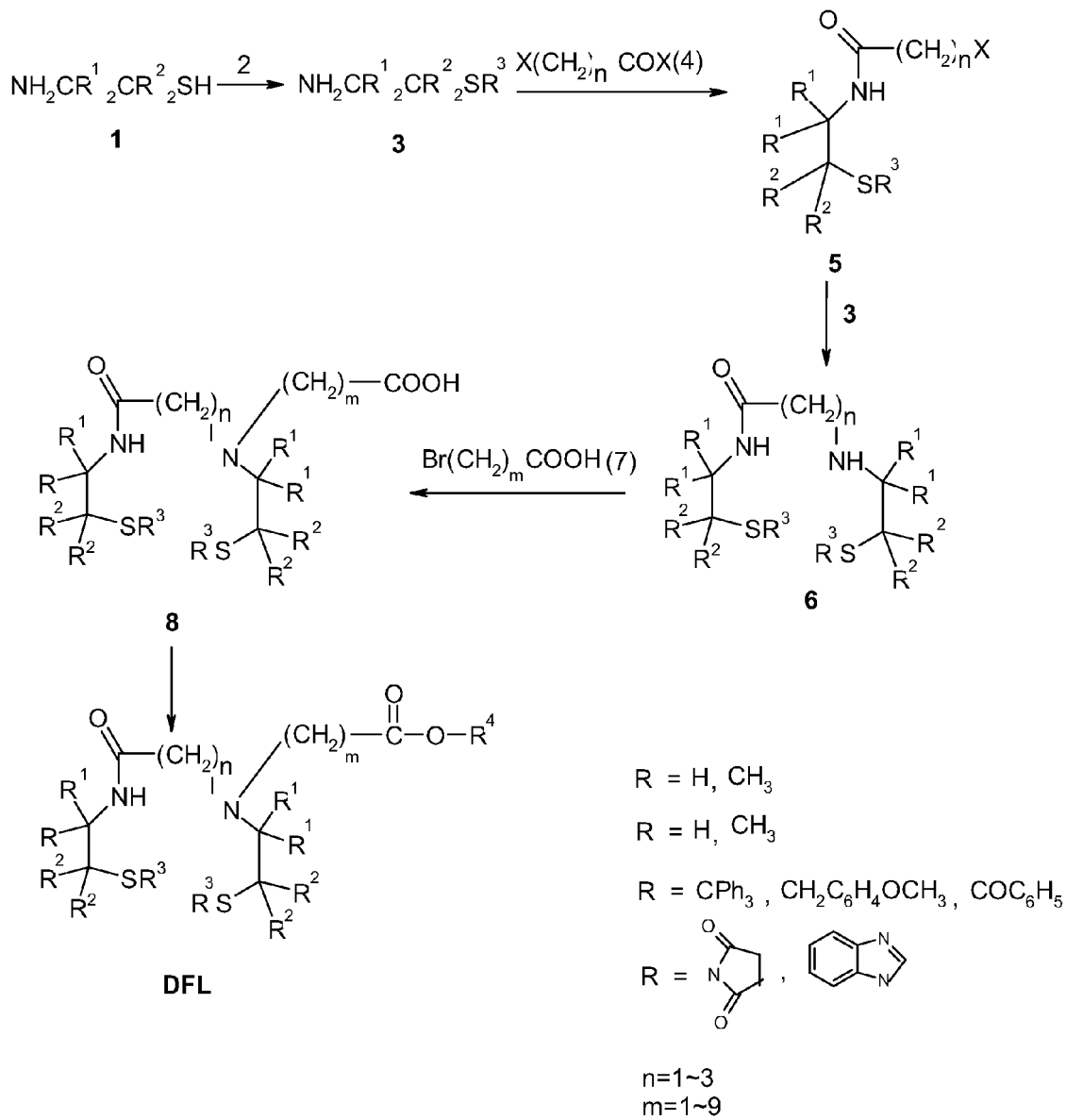
FIG. 1 is a schematic drawing showing manufacturing processes of an embodiment of a compound containing carboxylate ester and N2S2 ligand bi-functional groups according to the present invention.

A manufacturing method of the compound containing carboxylate ester and N2S2 ligand bi-functional groups according to the present invention includes the following steps (as shown in FIG. 1):

(1) reacting $NH_2CR^1{}_2CR^2{}_2SH$ with a protective agent to form $NH_2CR^1{}_2CR^2{}_2SR^3$;

(2) carrying out an amidation reaction between $NH_2CR^1{}_2CR^2{}_2SR^3$ and $X(CH_2)_nCOX$ to form

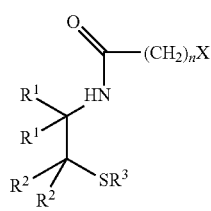

(3) undergoing a substitution reaction between

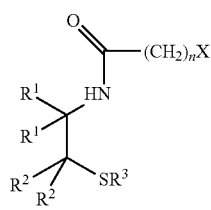

and $NH_2CR^1{}_2CR^2{}_2SR^3$ to form

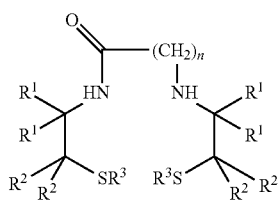

(4) carrying out a substitution reaction between

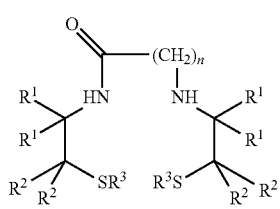

and $Br(CH_2)mCOOH$ to form

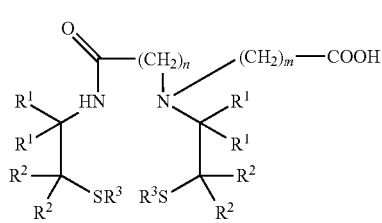

(5) dehydrating N,N'-dicyclohexyldicarbodiimide to get

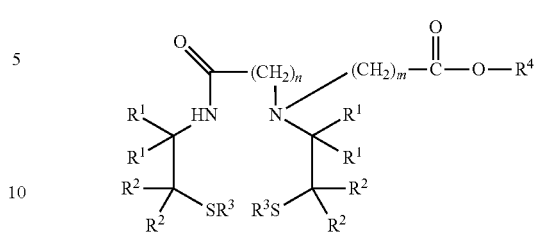

wherein $R^1=H, CH_3$; $R^2=H, CH_3$; $R^3=CPh_3$, $CH_2C_6H_4OCH_3$, $COC_6H_5$;

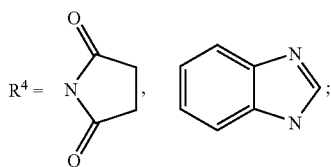

n=1~3; m=1~9 while X is halogen atom

In the step (1), the protective agent is triphenyl methanol. The step (1) further includes a step to dissolve in trichloromethane and then apply a heat reflow step in which boron trifluoride ethyl etherate complex is added as a catalyst. The step (2) further consists of a step of washing the organic phase and condensation under reduced pressure after the step of dissolving in trichloromethane. The step (3) further includes a step of dissolving in dichloromethane, adding triethylamine followed by a heat flow process and liquid chromatography for purification while the step (4) further includes a heat reflow step after addition of bromoacetic acid, triethylamine and acetonitrile, condensation under reduced pressure, and liquid chromatography for purification. The step (5) includes a step of adding N-hydroxysuccinimide, 1,3-dicyclohexyl-carbodiimide and tetrahydrofuran to form N,N'-dicyclohexyldicarbodiimide.

In the step (5), when n and m=1 and $$R^4 = \underset{O}{\underset{\|}{\overset{O}{\overset{\|}{N}}}}$$

, the compound containing carboxylate ester and N2S2 ligand bi-functional groups is Succinimidyl 3,6-diaza-5-oxo-3-[2-((triphenylmethyl)thio)ethyl]-8-[(triphenylmethyl)thio] octanoate, abbreviated as SOCTA.

Figure 2:
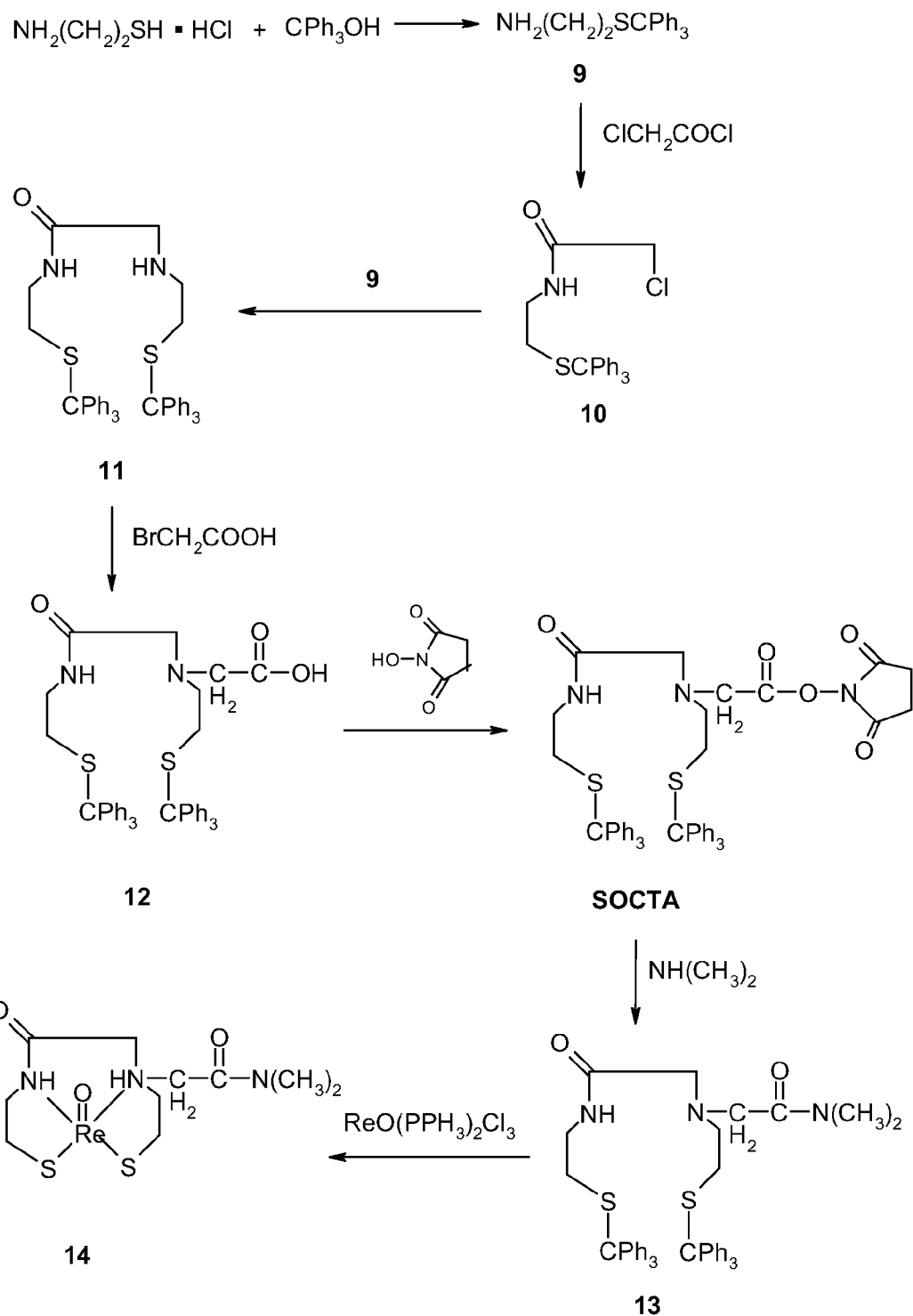
FIG. 2 is a schematic drawing showing manufacturing processes of SOCTA, and SOCTA labeled with amines and radioactive nuclides according to the present invention.

Take a compound with bi-functional groups-SOCTA (uc-cinimidyl 3,6-diaza-5-oxo-3-[2-((triphenylmethyl)thio) ethyl]-8-[(triphenylmethyl)thio]octanoate) as an example, refer to FIG. 2, a synthesis method of SOCTA, the amidation reaction of SOCTA with amines and the following complex reaction are described:

(1) synthesis of 1,2-[(Triphenylmethyl)thio]ethylamine9

Take 10 g (88.4 mmol) 2-thioethylamine hydrochloride, 22 g (85 mmol) triphenylmethanol, and 14 mL (99.7 mmol) triethylamine, all dissolve in 100 mL trichloromethane. Then apply a heat reflow step at 75° C. and slowly drop 30 mL (239 mmol) boron trifluoride ethyl ether complex into the solution and continue the heat reflow step for four hours. Next perform the condensation under reduced pressure, add methanol to dissolve, and condensed again. Add sodium bicarbonate solution and stir the solution. Then a white solid precipitate is obtained. After vacuum filtering, wash the obtained solid and dried to get 27.9 g (99%) solid compound 9.

IR (neat) ν 3381 ($NH_2$) $cm^{-1}$. $^1H$ NMR ($CDCl_3$) δ 7.42 (m, 3 H, Ph), 7.30 (m, 12 H, Ph), 2.58 (t, J=6.6 Hz, 2 H, $CH_2N$), 2.32 (t, J=6.6 Hz, 2 H, $CH_2S$), 1.45 (br, 2 H, $NH_2$). $^{13}C$ NMR ($CDCl_3$) δ 144.80, 192.52, 127.81 and 126.60 (Ph), 66.51 (CPh), 40.94 ($CH_2N$), 36.09 ($CH_2S$). MS m/z 319 ($M^+$), 243 ($M^+$–$C_6H_5$+1).

(2) synthesis of N-[2-((Triphenylmethyl)thio)ethyl]chloroacetamide 10

Take 10.63 g, (33.3 mmol) compound 9 and 5.6 mL (39.9 mmol) triethylamine, dissolve them in 80 mL trichloromethane. Slowly drop solution of 3.18 mL (39.9 mmol) chloroacetyl chloride dissolved in 10 mL trichloromethane into the mixture, cooling in ice. After dripping off, stir the solution at room temperature for two hours. Wash the organic phase by following solutions in sequence: 1N Hydrochloric acid solution HCl (120 mL), saturated sodium carbonate aqueous solution (100 mL) and water (100 mL). After dehydration of the organic phase with $Na_2SO_4$, condense under reduced pressure to get yellow oil product 10 (12.67 g, 96%).

IR (neat) ν 3413 and 3306 (NH), 1662 (CO) $cm^{-1}$. $^1H$ NMR ($CDCl_3$) δ 7.41 (m, 3 H, Ph), 7.24 (m, 12 H, Ph), 6.48 (br, 1 H, NH), 3.97 (s, 2 H, $CH_2Cl$), 3.12 (q, J=6.3 Hz, 2 H, $CH_2N$), 2.43 (t, J=6.3 Hz, 2 H, $CH_2S$). $^{13}C$ NMR ($CDCl_3$) δ 165.63 (CO), 144.47, 129.48, 127.97 and 126.81 (Ph), 66.52 (CPh), 42.54 ($CH_2Cl$), 38.35 ($CH_2N$), 31.67 ($CH_2S$). MS m/z 397 and 395 ($M^+$), 243 (($CPh_3$)$^+$).

(3) synthesis of N-[2-((Triphenylmethyl)thio)ethyl] [2-((Triphenylmethyl)thio)ethyl-amino]acetamide 11

Dissolve 12.7 g (32 mmol) the compound 10 and 10.2 g (32 mmol) the compound 9 into 60 mL dichloromethane. Then add 6.7 mL (48 mmol) triethylamine followed by a heat flow process for two days. After cooling, wash with 60 mL Sodium hydrogen carbonate aqueous solution, and wash again with 60 mL water, take the organic layer. The organic phase is dried by $Na_2SO_4$, condensed and then purified by liquid chromatography ($SiO_2$, ethyl acetate: hexane=1:1) to get light yellow oil product 11 (12.9 g, 59.9%).

IR (neat) ν 3330 (NH), 1670 (CO) $cm^{-1}$. $^1H$ NMR ($CDCl_3$) δ 7.42 (m, 4 H, HNCO and Ph), 7.20 (m, 12 H, Ph), 3.07 (m, 4 H, $CH_2NCO$ and $CH_2CO$), 2.38 (m, 6 H, $CH_2NHCH_2CO$ and $CH_2S$), 1.94 (br, 1 H, $NHCH_2CO$). $^{13}C$ NMR ($CDCl_3$) δ 170.84 (CO), 144.61, 129.47, 127.88 and 126.69 (Ph), 66.72 and 66.65 (CPh$_3$), 51.62 ($CH_2CO$), 48.19 ($CH_2NHCH_2CO$), 37.70 ($CH_2NHCO$), 32.12 and 31.97 ($CH_2S$). MS m/z 243 (($CPH_3$)$^+$).

(4) synthesis of 3,6-Diaza-5-oxo-3-[2-((triphenylmethyl)thio)ethyl]-8-[(triphnyl-methyl) thio]octanoic acid 12

Take 10.1 g (14.9 mmol) compound 11, 2.2 g (15.8 mmol) bromoacetic acid, 3.13 mL (22.3 mmol) triethylamine and 30 mL acetonitrile and perform a heat reflow step at 85° C. overnight. After cooling, condensation under reduced pressure, dissolve the residual in 80 mL dichloromethane and wash with 80 mL water, remove the water phase. The organic phase is dehydrated by $Na_2SO_4$, condensed and purified by liquid chromatography ($SiO_2$, ethylacetate: hexane=1: 1) to get light yellow oil product 12 (6.5 g, 56.1%).

IR (neat) ν 3327 (NH), 1726 and 1634 (CO) $cm^{-1}$. $^1H$ NMR ($CD_3OD$) δ 7.40 (m, 3 H, Ph), 7.25 (m, 12 H, Ph), 3.21 (s, 2 H, $CH_2$), 3.11 (s, 2 H, $CH_2$), 2.30 (t, J=6.6 Hz, 2 H, C$H_2$NH), 2.52 (t, J=6.6 Hz, 2 H, $CH_2N$), 2.34 (t, J=6.6 Hz, 4 H, $CH_2S$). $^{13}C$ NMR ($CD_3OD$) δ 173.89 and 172.97 (CO), 146.11, 130.72, 128.96, 127.87 and 127.81 (Ph), 68.09 and 67.84 (CPh$_3$), 59.0, 55.86 and 55.13 ($CH_2$), 39.12 ($CH_2NH$), 32.70 and 31.01 ($CH_2S$). MS m/z 243 (($CPh_3$)$^+$).

(5) synthesis of Succinimidyl 3,6-diaza-5-oxo-3-[2-((triphenylmethyl)thio)ethyl]-8-[(triphenylmethyl) thio]octanoate (SOCTA)

Take 1.65 g (2.1 mmol) compound 12, add with 0.3 g (2.52 mmol) N-hydroxysuccinimide, 0.7 g (31.5 mmol) 1,3-dicyclohexylcarbodiimide, and 30 mL tetrahydrofuran, stir at room temperature overnight. Remove the solid percipitate by vacuum filtering and condense the solution under reduced pressure. The purify by liquid chromatography (SiO2, ethyl acetate) to get oil product SOCTA (1.79 g, 60.2%).

IR (neat) ν 3360 (NH), 1815, 1786, 1741 and 1674 (CO) $cm^{-1}$. $^1H$ NMR ($CDCl_3$) δ 7.37 (m, 4 H, NH and Ph), 7.21 (m, 12 H, Ph), 3.49 (s, 2 H, $CH_2$), 3.31 (s, 2 H, $CH_2$), 3.02 (q, J=6.6 Hz, 2 H, $CH_2NH$), 2.75 (s, 4 H, $CH_2CH_2CO$), 2.58 (t, J=6.6 Hz, 2 H, $CH_2N$), 2.36 (t, J=6.6 Hz, 2 H, $CH_2S$), 2.31 (t, J=6.6 Hz, 2 H, $CH_2S$). $^{13}C$ NMR ($CDCl_3$) δ 169.68, 168.56 and 165.63 (CO), 144.68, 144.50 129.52, 129.47, 127.96, 127.88, 126.78 and 126.65 (Ph), 66.94 and 66.68 (CPh$_3$), 57.96, 53.31 and 52.41 ($CH_2$), 38.07 ($CH_2NH$), 31.89 and 29.93 ($CH_2S$), 25.50 ($CH_2CH_2CO$). MS m/z 243 (($CPh_3$)$^+$).

Refer to FIG. 2, the experiment shows SOCTA conjugating with amino groups and radioactive nuclides:

(1) Synthesis of N,N-Dimethyl 3,6-diaza-5-oxo-3-[2-((triphenylmethyl)thio)ethyl]-8-[(triphenylmethyl) thio]octanamide 13

Dissolve 1.67 g (2.0 mmol) SOCTA and 10 mL (18.2 mmol) dimethyl amine in 30 mL trichloromethane and stir the solution at room temperature overnight. After being dried under reduced pressure, dissolve the residual with ethyl ether and purify by liquid chromatography ($SiO_2$, chloroform) to get oil product 13 (1.22 g, 80%).

IR (neat) ν 3341 (NH), 1673 and 1651 (CO) $cm^{-1}$. $^1H$ NMR ($CDCl_3$) δ 7.87 (t, J=6.6 Hz, 1, NH), 7.21-7.06 (m, 30 H, Ph), 3.19 (s, 2 H, $CH_2CO$), 3.09 (s, 2 H, $CH_2CO$), 3.04 (q, J=6.6 Hz, 2 H, $CH_2NHCO$), 2.82 (s, 3 H, $NCH_3$), 2.77 (s, 3, H, $NCH_3$), 2.64 (t, J=6.6 Hz, 2 H, $CH_2$ $CH_2NCH_2CO$), 2.39 (t, J=6.6 Hz, 2 H, $CH_2CH_2NHCO$), 2.26 (t, J=6.6 Hz, 2 H, C$H_2CH_2NCH_2CO$). $^{13}C$ NMR ($CDCl_3$) δ 171.17 and 169.67 (CO), 144.74, 144.70, 129.52, 129.49, 127.83, 126.63 and 126.60 (Ph), 66.69 and 66.54 (CPh), 58.39, 54.58, 53.97 and 37.98 ($CH_2$), 36.16 and 35.38 ($NCH_3$), 31.88 and 30.23 ($CH_2$). MS m/z 243 (($CPh_3$)$^+$).

(2) synthesis of [N-(2-thioethyl)-N-(2-thioethyl)-N-(N,N-dimethy carbamoylmethyl) aminoacetimido] oxorhenium(V) 14

Dissolve 0.63 g (0.83 mmol) compound 13, 0.87 g (1.0 mmol) $ReO(PPh_3)_2Cl_3$, and 0.4 mL (2.9 mmol) triethylamine in 50 mL methanol and heat the solution at 55° C. for 16 hours. After filtering, dry the solution under reduced pressure and dissolve the residue with trichloromethane. Wash with water and perform the liquid chromatography (SiO$_2$, chloroform: methanol=100:5) for purification to get reddish brown sticky product 14 (0.18 g, 45%).

IR (neat) v 1639 and 1614 (CO), 961 (ReO) cm$^{-1}$. $^1$H NMR (CDCl$_3$) δ 5.62 (d, J=15.0 Hz, 1 H, NCOCH$_2$N), 4.83 (dd, J=12.0 and 4.8 Hz, 1 H, CONCH$_2$CH$_2$), 4.66 (dd, J=15.0 and 2.4 Hz, 1 H, NCOCH$_2$N), 4.32 (m, 1 H, COCH$_2$NCH$_2$CH$_2$), 3.76 (m, 1 H, COCH$_2$NCH$_2$CH$_2$), 3.60-3.30 (m, 3 H, CONCH$_2$CH$_2$), 3.26-3.05 (m, 3 H, COCH$_2$NCH$_2$CH$_2$), 2.89 (s, 3 H, CH$_3$), 2.72 (s, 3 H, CH$_3$), 2.42 (d, J=17.1 Hz, 1 H, NCOCH$_2$N). $^{13}$C NMR (CDCl$_3$) δ 184.88 and 163.64 (CO), 68.29, 63.58, 54.28, 53.40, 47.98 and 40.69 (CH$_2$), 36.65 and 35.67 (CH$_3$). MS m/z 479 and 477 (M$^+$).

The experiment showing conjugation of SOCTA with amino groups and radioactive nuclides proves that the SOCTA compound in the compound containing carboxylate ester and N2S2 ligand bi-functional groups according to the present invention not only reacts with amino acids, peptides or proteins but also bonds with radionuclides such as ReO$^{3+}$ or TcO$^{3+}$. Thus it can be applied to labeling of proteins/peptides with Tc/Re or disease treatment. Moreover, the compound containing carboxylate ester and N2S2 ligand bi-functional groups has photostability so that it is easy to be operated and used under environment with light. Furthermore, there is no need to add auxiliary chelating agents during the processes so that both reaction processes and the cost are reduced.

Additional advantages and modifications will readily occur to those skilled in the art. Therefore, the invention in its broader aspects is not limited to the specific details, and representative devices shown and described herein. Accordingly, various modifications may be made without departing from the spirit or scope of the general inventive concept as defined by the appended claims and their equivalents.

What is claimed is:

1. A compound consisting of carboxylate ester and N2S2 ligand bi-functional groups consisting of:

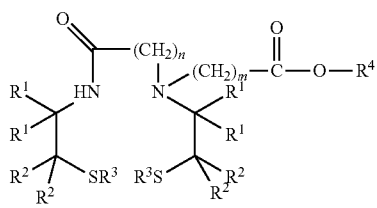

wherein R$^1$=H, CH$_3$; R$^2$=H, CH$_3$; R$^3$=CPh$_3$, CH$_2$C$_6$H$_4$OCH$_3$, COC$_6$H$_5$;

R$^4$= 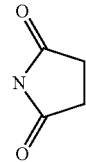

n=1~3 and m=1~9.

2. The compound as claimed in claim 1, wherein when both n and m=1, and R$^4$=

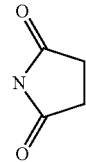

the compound is Succinimidyl 3,6-diaza-5-oxo-3-[2-((triphenylmethyl)thio)ethyl]-8-[(triphenylmethyl)thio]octanoate, abbreviated as SOCTA.

3. A manufacturing method of the compound consisting of carboxylate ester and N2S2 ligand bi-functional groups consisting of the steps of:

(1) reacting NH$_2$CR$^1_2$CR$^2_2$SH with a protective agent to form NH$_2$CR$^1_2$CR$^2_2$SR$^3$ (2) carrying out an amidation reaction between NH$_2$CR$^1_2$CR$^2_2$SR$^3$ and X(CH$_2$)$_n$COX to form

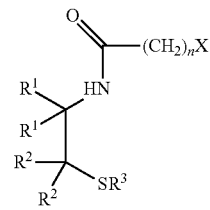

(3) undergoing a substitution reaction between

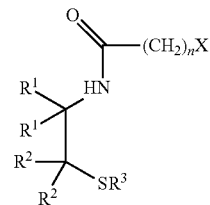

and NH$_2$CR$^1_2$CR$^2_2$SR$^3$ to form

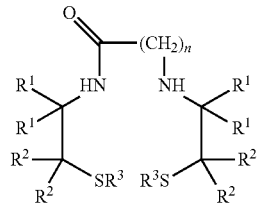

(4) carrying out a substitution reaction between

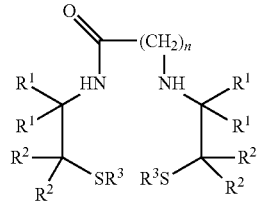

and Br(CH$_2$)mCOOH to form

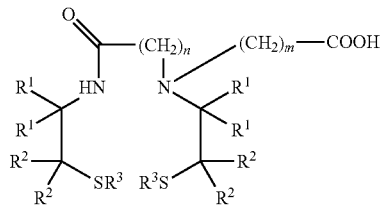

(5) dehydrating N,N'-dicyclohexyldicarbodiimide to get

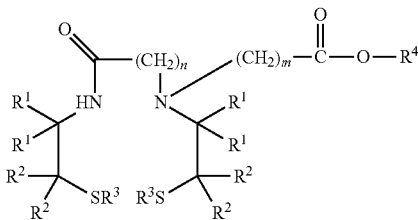

wherein R$^1$=H, CH$_3$; R$^2$=H, CH$_3$; R$^3$=CPh$_3$, CH$_2$C$_6$H$_4$OCH$_3$, COC$_6$H$_5$;

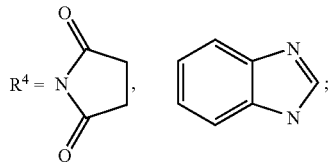

n=1~3; m=1~9 while X is halogen atom.

4. The method as claimed in claim 3, wherein the protective agent is triphenyl methanol.

5. The method as claimed in claim 3, wherein the step (1) further consist of a heat reflow step after dissolving NH$_2$CR$^1$$_2$CR$^2$$_2$SH and the protective agent are in trichloromethane.

6. The method as claimed in claim 5, wherein in the heat reflow step, boron trifluoride ethyl etherate complex is added as a catalyst.

7. The method as claimed in claim 3, wherein the step (2) further consists of a step of washing an organic phase and then being condensed under reduced pressure after dissolving NH$_2$CR$^1$$_2$CR$^2$$_2$SH$^3$ and X(CH$_2$)$_n$COX are dissolved in trichloromethane.

8. The method as claimed in claim 3, wherein the step (3) further consists of a step of dissolving NH$_2$CR$^1$$_2$CR$^2$$_2$SH$^3$ and

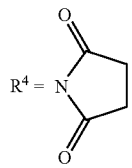

in dichloromethane, and then adding triethylamine followed by a heat flow process and liquid chromatography for purification.

9. The method as claimed in claim 3, wherein the step (4) further consists of a heat reflow step after adding bromoacetic acid, triethylamine and acetonitrile, then being condensed under reduced pressure, and then being purified by liquid chromatography.

10. The method as claimed in claim 3, wherein the step (3) further consists of a step of adding N-hydroxysuccinimide, 1, 3-dicyclohexylcarbodiimide and tetrahydrofuran to form N,N'-dicyclohexyldicarbodiimide.

11. The method as claimed in claim 3, wherein in the step (5), when both n and m=1, R$^4$=

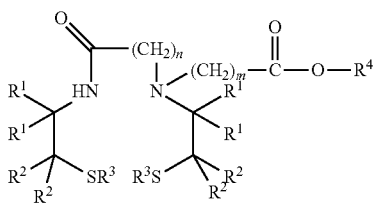

consisting of carboxylate ester and N2S2 ligand bi-functional groups is Succinimidyl 3,6-diaza-5-oxo-3-[2-((triphenylmethyl)thio)ethyl]-8-[(triphenylmethyl)thio]octanoate, abbreviated as SOCTA.

* * * * *